US006967080B1

(12) United States Patent
Loevborg

(10) Patent No.: US 6,967,080 B1
(45) Date of Patent: Nov. 22, 2005

(54) PROTEINS WITH CHANGED EPITOPES AND METHODS FOR THE PRODUCTION THEREOF

(75) Inventor: Uffe Loevborg, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/056,343

(22) Filed: Apr. 7, 1998

Related U.S. Application Data

(60) Division of application No. 08/346,590, filed on Nov. 29, 1994, now Pat. No. 5,766,898, which is a continuation of application No. 08/050,172, filed on Apr. 16, 1993, now abandoned, which is a continuation of application No. PCT/DK91/00382, filed on Dec. 5, 1991.

(30) Foreign Application Priority Data

Dec. 5, 1990 (EP) ................................. 90610092

(51) Int. Cl.[7] .......................... G01N 33/53; C12P 9/00; C12N 15/74
(52) U.S. Cl. ...................... 435/7.1; 435/69.1; 435/183; 435/471
(58) Field of Search ............................. 435/417, 183, 435/189, 198, 209, 212, 232, 69.1, 252.3, 435/320.1, 471, 7.1; 424/94.1, 94.64; 514/2; 536/23.2, 23.5

(56) References Cited

U.S. PATENT DOCUMENTS

| 4,560,651 | A | * | 12/1985 | Nielsen et al. ................. 435/95 |
| 4,894,443 | A | * | 1/1990 | Greenfield et al. .......... 530/388 |
| 4,945,043 | A | * | 7/1990 | Gerber ........................... 435/7 |
| 4,970,300 | A | * | 11/1990 | Fulton et al. ................. 530/383 |
| 5,098,833 | A | * | 3/1992 | Lasky et al. ................. 435/69.1 |
| 5,109,113 | A | * | 4/1992 | Caras et al. ................. 530/350 |
| 5,223,409 | A | * | 6/1993 | Ladner et al. ............. 435/69.6 |
| 5,258,287 | A | * | 11/1993 | Baxter et al. .............. 435/69.1 |
| 5,766,898 | A | * | 6/1998 | Loevborg ................... 435/471 |
| 6,218,165 | B1 | * | 4/2001 | Estell et al. ................. 432/221 |

FOREIGN PATENT DOCUMENTS

WO  WO 89/06279  * 7/1989
WO  WO 01/59130 A3  * 8/2001

OTHER PUBLICATIONS

Hopp, T. P., et al., Proceedings of the National Academy of Sciences, U.S.A., vol. 78, "Prediction of protein antigenic determinants from amino acid sequences", pp. 3824-3828.*

Luo, L., et al., Virology, vol. 163, "Point mutations in glycoprotein gene of vesicular stomatitis virus (New Jersey serotype) selected by resistance to neutralization by epitope-specific monoclonal antibodies", pp. 341-348.*

Choo, S. Y., et al., Human Immunology, vol. 21, "Molecular analysis of the variant alloantigen HLA-B27d (HLA-B*2703) identifies a unique single amino acid substitution", pp. 209-219.* de la Cruz, V. F., et al., The Journal of Biological Chemistry, vol. 263, "Immunogenicity and epitope mapping of foreign sequences via genetically engineered filamentous phage", pp. 4318-4322.*

Bolwell, C., et al., Journal of General Virology, vol. 70, "Epitope mapping of foot-and-mouth disease virus with neutralizing monoclonal antibodies", pp. 59-68.*

Keil, W., et al., Virology, vol. 170, "Epitope mapping by deletion mutants and chimeras of two vesicular stomatitis virus glycoprotein genes expressed by a vaccinia virus vector", pp. 392-407.*

Collins et al., Clinical and Experimental Allergy, vol. 26, pp. 36-42 (1996).

Naver et al., Scand. J. Immunol., vol. 41, pp. 443-448 (1995).

* cited by examiner

Primary Examiner—Ponnathapura Achutamiurthy
Assistant Examiner—William W. Moore
(74) Attorney, Agent, or Firm—Elias J. Lambiris

(57) ABSTRACT

The present invention relates to methods for modifying proteins by mapping one or more epitopes of the protein and altering the amino acid sequence of one or more epitopes of the protein in order to make the protein less immunogenic.

8 Claims, 3 Drawing Sheets

PROTEINS WITH CHANGED EPITOPES AND METHODS FOR THE PRODUCTION THEREOF

CROSS-REFERENCE TO RELATED APPLICATIONS

This application is a divisional application of Ser. No. 08/346,590 filed Nov. 29, 1994, and now issued as U.S. Pat. No. 5,766,898, which is a continuation of Ser. No. 08/050, 172 filed Apr. 16, 1993, and now abandoned, which is a a continuation of national application of PCT/DK91/00382 filed Dec. 5, 1991 and claims priority under 35 U.S.C. 119 of application serial no. EP 90610072.2 filed Dec. 5, 1990, the contents of which are fully incorporated herein by reference.

FIELD OF THE INVENTION

This invention relates to methods for modifying proteins, especially enzymes that are used industrially, and proteins used in medicine, and the modified proteins produced thereby, compositions containing such protein variants, and the use of the variants in various fields, including medicine. According to the invention the proteins are epitope mapped using immunological and proteochemical methods and eventually their amino acid sequence is changed through genetic engineering thereby changing their immunological activity in order to make them less immunogenic and thereby reduce the risk of provoking allergic responses in animals, including man, subjected to exposure to the enzymes of the present invention.

BACKGROUND OF THE INVENTION

Various proteins, such as enzymes are used increasingly in industry and householding. Being proteins they will be able to stimulate an immunological response in man and animals.

Other proteins, such as hormones are used increasingly in medicine for the treatment and/or diagnosis of various conditions of illness and disease, whereby these proteins are injected into or otherwise presented to the immune system of animals, including man.

Depending on the way of presentation the stimulation can lead to production of various types of antibodies, and to a cellular response too. Of these routes at least one, being the one type of antibody can have adverse effect in man and animals. The production of IgE and maybe IgG4 can lead to an allergic state, giving symptoms like f.ex. rhinitis, conjunctivitis or other.

It cannot be excluded that other immunologically based adverse reactions will be seen with the increased use of these proteins.

These drawbacks in the use of proteins have been known for many years and various solutions have been used for solving these.

Within the field of industrial enzymes the most frequently used method for avoiding problems with allergic reactions from exposure to the products has been confectioning the enzymes in various ways by immobilizing, granulating and coating the enzymes thereby avoiding any release of the proteinaceous material during normal handling and storage.

However, this solution poses various problems in relation to bringing the enzyme into contact with the material with which it is meant to interact, such as bringing the enzyme into solution etc., and also some release of the enzyme may occur provoking an allergic reaction in subjects sensitive to an exposure.

Within the field of medicine a much used method has been to use proteins of especially human or corresponding animal origin or at least of the same primary structure as the human (or the animal in question) protein.

This has proven to be successful in many instances, but it is not always possible to establish the existence of an animal equivalent to the protein in question, or it has been found that certain modified proteins possess certain advantages over the native protein. In such instances the risk of provoking an allergic response in the subject receiving treatment or being diagnosed exists.

Consequently a need exists for developing proteins that provoke less or no allergic reactions, while still retaining their original activity to a degree where they still are functional and may be used according to their original intent.

Those parts of a protein molecule that are recognized and bound immunologically are called epitopes. For molecules in the range of f.ex. 30000 Daltons there might be as many 12 epitopes.

Epitopes are being bound by immunological cells and by antibodies. Some epitopes are more important than other, these are called major in contrast to minor epitopes.

It has been found that slight changes in the epitopes will affect the binding strength in these bindings (Walsh, B. J. and Howden, M. E. H. (1989): A method for the detection of IgE binding sequences of allergens based on a modification of epitope mapping, Journal of Immunological Methods, 121, 275–280; Geysen, H. M., Tainen, J. A., Rodda, S. J., Mason, T. J., Alexander, H., Getzoff, E. D. and Lerner, R. A. (1987): Chemistry of Antibody Binding to a Protein. Science. 135, 1184–90; Geysen, H. M., Mason, T. J. and Rodda, S. J. (1988): Cognitive Features of Continuous Antigenic Determinants. Journal of molecular recognition. 1, 32–41.

This may result in a reduced importance of such a changed epitope, maybe converting it from a major to a minor epitope, or the binding strength may even be decreased to the level of high reversibility, i.e. no efficient binding. This phenomenon may be called epitope loss.

The above investigations were all performed on synthesized peptides mimicking the epitopes in question and variants thereof in order to establish the relative importance of the amino acid residues in the epitope being investigated, and consequently these investigations do not prove any effects to the epitopes in their native environment as parts of the complete protein, where phenomena only found in the tertiary structure of the protein, such as folding or the establishment of salt bridges etc., are in function.

SUMMARY OF THE INVENTION

The object of the invention is to provide for methods for selecting where in the amino acid sequence of a protein to modify in order to obtain protein variants evoking a reduced immunological response, and these protein variants.

The present invention consequently in a first aspect relates to a method of producing protein variants evoking a reduced immunogenic response in animals including man in comparison to the response evoked by its parent protein.

For this the protein is epitope mapped using immunological and proteochemical methods, and the various epitopes are determined and characterized.

Subsequent to this at least one of said epitopes is changed through mutation of a DNA molecule coding for the expression of said parent protein, or through synthesis of a DNA molecule coding for the expression of said variant protein. this is performed by using well established techniques known in the art of protein engineering.

The mutated or constructed DNA molecule is subsequently inserted into a vector for transformation of transfection into a suitable host, wherein said vector is functional or whereby said mutated or constructed DNA molecule is integrated functionally into the genome of said host, and the protein variant of interest is expressed in the host.

Finally the protein variant is recovered and purified.

In a second aspect the invention relates to the proteins produced by the above method. Under this aspect industrial enzymes, such as detergent enzymes, e.g. proteases, lipases, cellulases, amylases, or oxidases, process enzymes, e.g. amylases, lyases, lipases, or cellulases, medicinal proteins, e.g. hormones, e.g. insulin, HCG, or growth hormone, or medicinal enzymes, e.g. factor V, factor VII, factor VIII, or other proteins, e.g. interleukins, or interferons, are of special interest.

In a third aspect the invention relates to compositions comprising the proteins of the second aspect, such as detergent compositions, or compositions for use in preventive and/or alleviating therapy and/or diagnosis of various conditions in the animal body, including man.

In a fourth aspect the invention relates to the use of such compositions in preventive and/or alleviating therapy and/or diagnosis of various conditions in the animal body, including man.

BRIEF DESCRIPTION OF THE DRAWING

The invention will be explained and illustrated in further detail in the following parts of the specification including the specific examples and the appended drawing, wherein.

DETAILED DESCRIPTION OF THE INVENTION

Figure 1:
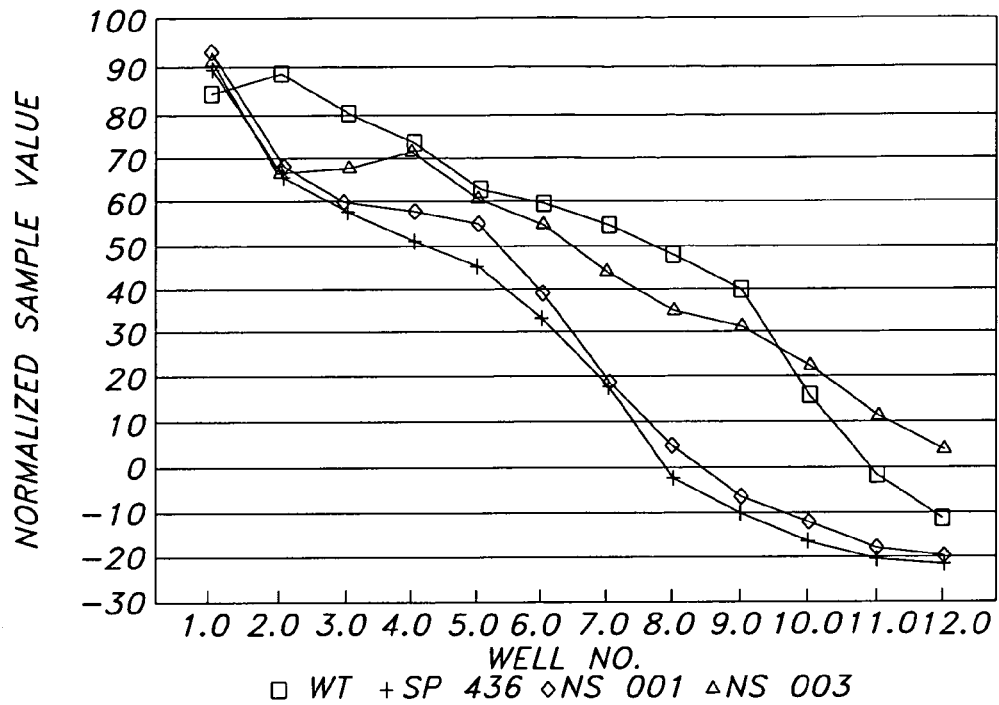
FIGS. 1 to 6 show plots of the binding of a number of enzyme variants to a reference antiserum as a function of their concentration
Figure 2:
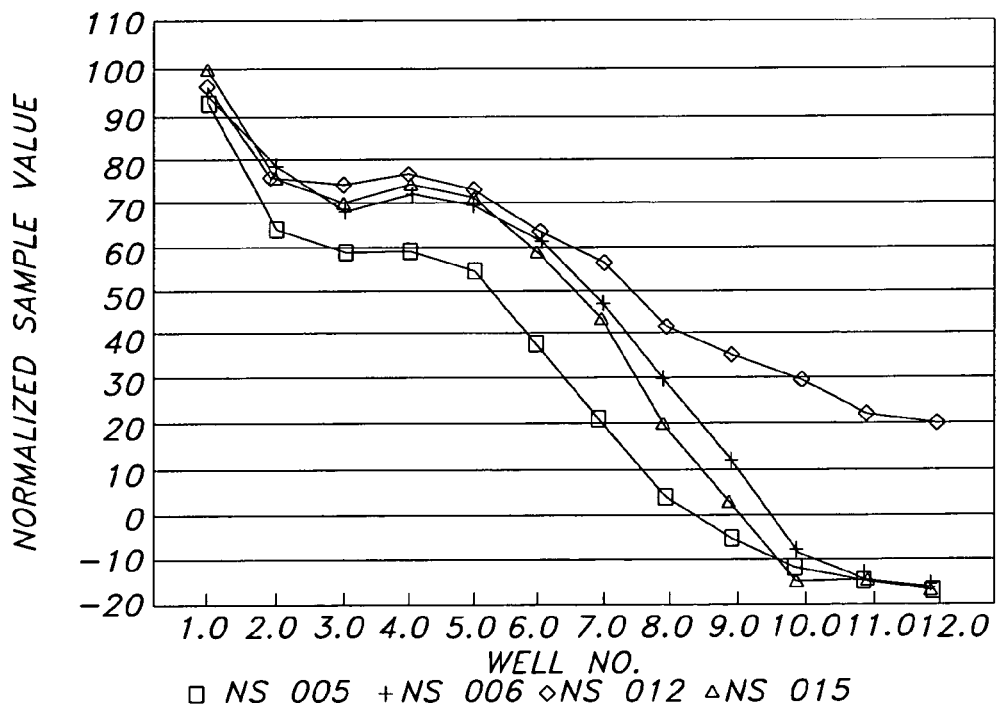
Figure 3:
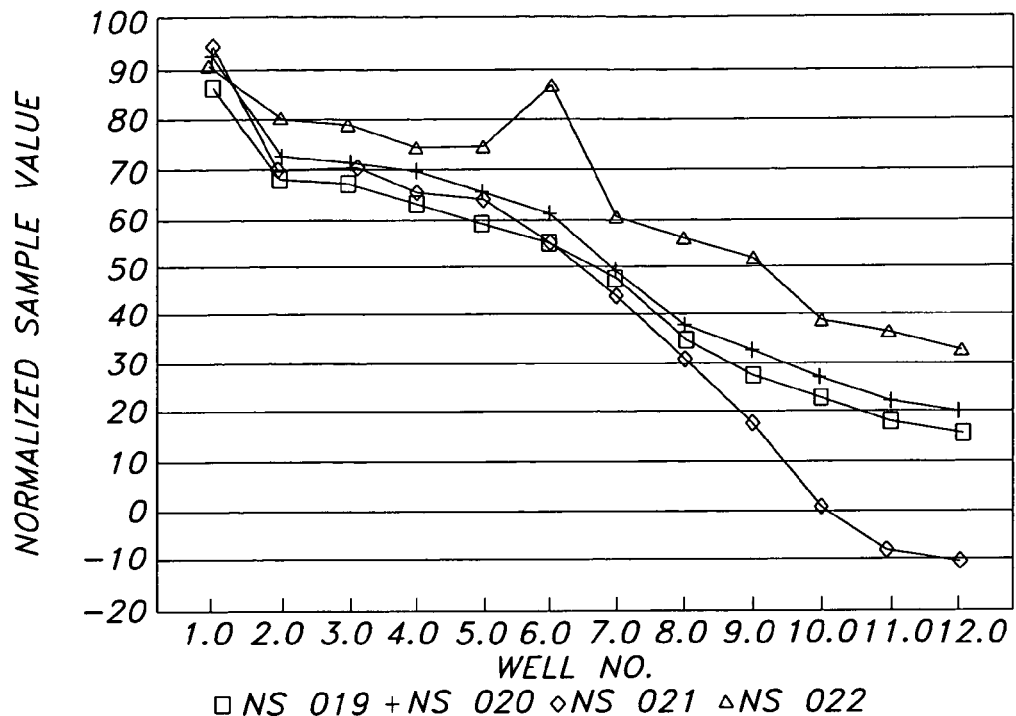

According to the first aspect of the invention epitope mapping is used to locate and characterize the various epitopes functionally present in a protein. Thereafter this information is used for selecting which amino acid residues in the epitopes should be changed.

When the changes have been implemented through the now well established techniques of genetic engineering, and the protein variants have been produced, immunological and proteochemical techniques are used to analyze the new protein variants and determine whether the changes have led to switches from major to minor epitopicity or even to epitope loss.

This information is again used to decide whether the protein variant(s) produced correspond to demands established for the protein, or, whether more or other changes have to be implemented.

Through the invention it has thus been made possible to produce proteins, especially industrial enzymes and medicinal proteins that will present a reduced immunologic, such as allergenic, potential risk to the environment and animals subjected to exposure to the protein(s) in question.

The protein or enzyme variants of the invention will therefore present lower risk to man (and animals) be it in the production, usage or to the environment.

In performing protein mapping the protein of interest (called the reference protein) and variants thereof, made by genetic engineering of by chemical modification, are used for the production of antibodies. Antibodies can be polyclonal (like antisera) recognizing many epitopes in an antigen and cross reacting with other often related antigens, monospecific recognizing a single antigen, epitope monospecific recognizing a single epitope, or monoclonal recognizing a single epitope and produced through fusion of cells producing the antibody and immortal cells, such as carcinoma cells.

Polyclonal antibodies will react to the protein antigen in a polyspecific manner, i.e. there will be many specificities each reacting with each own epitope in the antigen or showing different reactivities to different related epitopes. Also, polyclonal antibodies will often cross-react with related antigens. Monospecific antibodies are polyclonal antibodies isolated according to their specificity for a certain antigen, such monospecific antibodies will normally only be specific to a very limited number of epitopes, and often only specific to one epitope.

Epitope mono specific antibodies are polyclonal antibodies isolated according to their specificity for a certain epitope. Such epitope mono specific antibodies will only be specific to one epitope, but they will often be produced by a number of antibody producing cells, and are consequently not identical.

Monoclonal antibodies are epitope-specific antibodies produced by the now well established technique of cell fusion between an antibody producing cell and an immortal cell. All monoclonal antibodies produced by one clone are identical.

The antibodies produced can bind the immunizing protein antigen. Furthermore, if fully or partially identical epitopes exist in the other proteins, the antibody will be able to bind to these too. If there is complete identity the recognition and binding will be identical. If there is partly identical epitopes the recognition will be different and the binding strength will be lower. If the epitope is not present the antibody will not bind.

The mapping using polyclonal antibodies, can be divided into two phases:

i) Measure the reactivity of the antibody preparations toward all proteins of interest.

ii) Measure the reactivity left over to react with one antigen after reaction with another.

The results from (i) will provide information about the immunogenic and allergenic potential of the variants investigated. According to this some variants exhibiting a reduced potential could prove to be interesting protein variants, whereas others exhibiting an increased potential are deemed not to be interesting from an immunological viewpoint.

The results from (ii) will provide information concerning:

iia) changes in epitope(s) showing which epitopes are more or less immunogenic/allergenic, iib) loss of epitope(s) (even the highest concentration of one antigen will not eradicate all reactivity to reference antigen), or iic) establishment of new epitope(s) (even the highest concentration of reference antigen will not eradicate all reactivity to a variant).

From this information it can be decided which variants can be used for the production.

The selected protein variants may be produced by methods which by now are well known to the person skilled in the art of protein engineering, and described in numerous publications, such as International Publication No. WO/06279 (NOVO INDUSTRI A/S), and International Patent Application No. PCT/DK90/00164 (NOVO-NORDISK A/S) for both of which relevant sections are hereby incorporated in their entirety by reference.

EXAMPLES

The reference protein antigen chosen was SP436, a variant of the alkaline protease, subtilisin 309, whose construction and production is described in detail in the above mentioned International Publication No. WO/06279 (NOVO INDUSTRI A/S), where it was designated (i). The SP436 variant comprises in respect of the wild type subtilisin 309 two changes in the amino acid sequence, i.e. G195E+M222A. International Patent Application No. PCT/DK90/00164 (NOVO-NORDISK A/S) shows the production of further variants made by genetic engineering. The wild type enzyme is produced by normal fermentation, and the antibodies are polyclonal from rat.

The SP436 molecule is a protein comprising 269 amino acid residues, and it has in comparison to the well known subtilisin BPN' 6 deletions. For further reference to the amino acid sequence of various subtilisin reference is again made to International Publication No. WO/06279 (NOVO INDUSTRI A/S), and International Patent Application No. PCT/DK90/00164 (NOVO-NORDISK A/S), wherein the amino acid sequences for a number of proteases, a numbering system for subtilisin enzymes based upon the sequence of the subtilisin BPN', and a notation for indicating changes in the amino acid sequences are indicated. The numbering and notation therefrom will be followed throughout this specification and appended claims.

Immunizations.

Rats were selected as test animal due to the fact that according to the literature these are the only normal laboratory animal that are capable of binding human IgE onto its mast and basophile cell membranes, and at the same time having IgE that will bind to human mast and basophile membranes.

The animals were divided into 12 groups each of 3 rats. For the immunizations the wild type (wt) subtilisin 309 and 11 variants thereof were selected. These are indicated in TABLE I below:

TABLE I

Subtilisin 309 variants used for immunization

| Grp No. | "Variant" | Adjuvant | Change in respect of wt |
|---|---|---|---|
| 1 | SP436 | Freund | G195E+M222A<br>p   - u   u |
| 2 | S001 | — | G195E<br>p   - |
| 3 | S003 | — | R170Y<br>+   p |
| 4 | S005 | — | K251E<br>+   - |
| 5 | S015 | — | K235L<br>+   u |
| 6 | S026 | — | E136R<br>-   + |
| 7 | S033 | — | E271Q<br>-   p |
| 8 | S006 | — | H120D<br>+   - |
| 9 | S020 | — | H120D+R170Y+G195E+K235L+K251E<br>+  - +  p p  - +  u +  - |
| 10 | S023 | — | *36D+H120D+R170Y+G195E+K235L<br>m - +  - +  p p  - +  u |

TABLE I-continued

Subtilisin 309 variants used for immunization

| Grp No. | "Variant" | Adjuvant | Change in respect of wt |
|---|---|---|---|
| 11 | S028 | — | D181N<br>-  p |
| 12 | WT | — | |

-: negatively charged
+: positively charged
p: polar
u: unpolar
m: missing(deletion)

The injected quantity was invariably 30 μg/animal/immunization. Each animal received 6 injections.

All 12 selected proteins were injected once in Freunds Complete Adjuvant, once in Freunds Incomplete Adjuvant and four times in NaCl 0.9%.

Blood was harvested one week after each immunization except for the final exsanguination, which followed 5 days after the last immunization.

After clotting, the sera from all three animals in each group were pooled.

The analytical work described in the present report was on the 12 sera pools after the third blood harvest.

Analysis.

The analytical work was performed in two series of analysis, A and D, both of which are ELISA techniques.

Series A:

One protein is used for coating the wells of one or more ELISA-plates. This protein can be the native (wildtype) or a variant.

The 12 different sera pools in this analysis are incubated in the coated wells. The sera have all been raised against different proteins. If the variants are similar the sera are expected to be similar in their reactivity pattern too. Each sera pool is tested in a dilution series in its own series of wells.

The potential binding of rat antibodies is visualized through binding of peroxidase labelled anti-rat antibodies.

If rat antibodies were bound to the enzyme coating, they will be bound in proportional manner by the peroxidase labelled anti-rat antibodies.

The presence of colour in this way gives a proportional visual and measurable indication of presence of enzyme specific rat antibodies.

In a short step by step sequence the setup is:
1) Enzyme coating of solid phase.
2) Albumin blocking of residual binding spots on solid phase.
3) Incubating sera in dilution series, enzyme active antibodies being bound to the coated enzyme.
4) Peroxidase labelled anti rat(IgX) antibodies.
5) Development of colour.
6) Determination.

The 12 sera groups were tested for reactivity towards one kind of protein (i.e. wt or variant) according to the above set-up. One by one different proteins were tested with the 12 sera groups.

The response was compared to the sera group originally immunized with the given protein, i.e. the reference.

The results give information on antibody recognizability of the individual proteins, Division can be made into three kinds of reactivity relative to the reference, i.e. same/higher/ lower reactivity. See TABLE II below. Because of the assay design the phenomena of epitope loss and/or epitope change (to give a decrease in binding strength) are indistinguishable from each other.

Sera were tested in dilution series, first dilution 20 to 800 times, depending on sera strenght, and from this dilution in two-fold series. Phosphate buffer including blocking agent BSA and detergent.

TABLE II

SERIES A: AN OVERVIEW OF RESULTS

| Variant: | Sera group no.: | | | | | | | | | | | | REF. GRP NO: |
|---|---|---|---|---|---|---|---|---|---|---|---|---|---|
| | 1 | 2 | 3 | 4 | 5 | 6 | 7 | 8 | 9 | 10 | 11 | 12 | |
| IgG | Selected dilution for all: 1280× | | | | | | | | | | | | |
| WT | 850 | 1152 | 1745 | 2486 | 2638 | 429 | 2361 | 2020 | 1186 | 1500 | 2004 | 977 | 12 |
| SP436 | 276 | 867 | 1933 | 2279 | 2832 | 287 | 1956 | 2526 | 1926 | 2491 | 2547 | 134 | 1 |
| S003 | 1265 | 1505 | 2614 | 2449 | 2079 | 218 | 1613 | 3178 | 1890 | 2146 | 2442 | 62 | 3 |
| S005 | 1600 | 1600 | 2097 | 2100 | 2580 | 237 | 1900 | 3435 | 2699 | 3075 | 2066 | 89 | 4 |
| S023* | 2034 | 1295 | 2696 | 2700 | 2736 | 332 | 1469 | 2326 | 1754 | 2968 | 1716 | 115 | 10 |
| S001 | 1119 | 1204 | 1652 | 1941 | 2502 | 285 | 1762 | 2836 | 2359 | 1701 | 2262 | 45 | 2 |
| S026 | 888 | 944 | 1544 | 1721 | 2415 | 615 | 1556 | 2785 | 1332 | 1147 | 1646 | 40 | 6 |
| SP458 | 1111 | 930 | 1287 | 1600 | 2213 | 193 | 2129 | 2596 | 1278 | 1323 | 2052 | 33 | none |
| IgE | Selected dilution for all: 160× | | | | | | | | | | | | |
| WT | 1017 | 1091 | 1216 | 1355 | 1396 | 460 | 1181 | 1786 | 1209 | 1264 | 1473 | 577 | 12 |
| SP436 | 341 | 680 | 1066 | 1143 | 1251 | 291 | 858 | 1185 | 1025 | 1350 | 1355 | 92 | 1 |
| S003 | 1135 | 1398 | 1452 | 1561 | 1726 | 646 | 1283 | 1693 | 1352 | 1499 | 1532 | 141 | 3 |
| S005 | 1006 | 1003 | 1316 | 1654 | 1672 | 412 | 1182 | 1909 | 1409 | 1587 | 1188 | 105 | 4 |
| S023 | 1117 | 1247 | 1500 | 1484 | 1241 | 333 | 940 | 1317 | 1460 | 1441 | 1398 | 56 | 10 |
| S001 | 836 | 1059 | 1298 | 1228 | 1490 | 324 | 1043 | 1509 | 1174 | 1172 | 1309 | 124 | 2 |
| S026 | 780 | 1033 | 1325 | 1374 | 1585 | 568 | 1205 | 1402 | 827 | 996 | 1188 | 103 | 6 |
| SP458 | 774 | 850 | 1092 | 1145 | 1517 | 388 | 1281 | 1289 | 790 | 1000 | 1205 | 83 | none |

*S023: sera 1 through 7 is multiplied with 1.5 to compare sera 8 through 12.

The IgG response (TABLE II) shows three effects
1) Each sera group (except anti-SP436) reacts stronger with its own immunogen than with any of the other. Especially sera no 12 (anti-wt) show dramatic lower response to other proteins.
2) Some sera give in general higher responses than other.
This last feature can become very important together with the IgG and IgE distribution. Anyhow, it cannot be excluded to belong to some individuality in the responding animals. Such a feature is often expressed when only few animal sera are pooled (like in this case, three).
3) There is a heteroclitic effect for each of the tested proteins except S023. This means that sera from animals immunized with a protein that is not the test protein, will react stronger than the sera coming from animals immunized with the test protein (horizontal values).
This is a characteristic feature also seen in work with small synthesized peptides that are used to produce antibodies to native (larger) protein. Here it is explained by differences in conformation being in favour of the native molecule.
The IgE response (TABLE II) show effects comparable to (1), (2), and (3) mentioned for the IgG response.
Switch from one immunizing protein to another similar protein will for all except SP436 give lower IgG and IgE response. Switch from SP436 to another will increase this very signal, but only to a level comparable to the ones otherwise seen. Furthermore there is a heteroclitic effect, which will be further discussed in connection with the following series D.

Series A:
Selected seras were tested with one and the same variant in each analysis. The variants were used for solid phase coating at a concentration of 50 µg/ml (phosphate buffer), this gave a near-monolayer immobilization. Residual binding spots on the surface were blocked by bovine serum albumin (=BSA).

Tracing performed by bound antivariant-antibody by mouse-anti-rat antibodies that are conjugated to peroxidase. (Kem-En-Tec cat. no. Y 3300 diluted 1000× in same buffer as used for seras).
Visualization was obtained through enzymatic reaction of peroxidase on OPD-substrate that is turning colored proportionally to peroxidase present, which is proportional to rat anti variant antibodies present.
Sera having high potential for reaction will give higher response than others, and this will make estimation of strenght and mutual reactivity possible.

4.A.4. Series A, Analysis 2+3
Analysis was performed as decribed under methods. Calculation of dilutions giving equal response, and "normalizing" these to the reference (i.e. the reaction of the individual sera with its immunising variant).
A low figure means the sera cannot be diluted as much as the reference, and a high figure that the sera can be diluted more than the reference. 49 therefore means that the serum can be diluted only 0.49 times the reference reaction, e.g. 490×for the sample in comparison to the reference 1000×.
Results from these experiments are indicated in TABLE III below:

TABLE III

SERIES A (analysis 2 + 3) DATA EXTRACTION

| AMINO ACID EXCHANGE: | FORWARD EXCHANGE: | REVERSE EXCHANGE: | RESPONSE TYPE: |
|---|---|---|---|
| G195E | 53 | 53 | A |
| R170Y | 84 | 65 | A |
| D181N | 164 | 24 | B |
| K235L | 114 | 56 | B |
| E136R | 80 | 53 | B |
| E271Q | 96 | 48 | B |
| H120D | 100 | 36 | B |
| E251K | 59 | 91 | C |

TABLE III-continued

SERIES A (analysis 2 + 3) DATA EXTRACTION

| AMINO ACID EXCHANGE: | FORWARD EXCHANGE: | REVERSE EXCHANGE: | RESPONSE TYPE: |
|---|---|---|---|
| G195E + M222A | 67 | 49 | A |
| E195G + R170Y | 126 | 77 | B |
| E195G + E136R | 106 | 50 | B |
| Y170R + E136R | 75 | 79 | A |
| E251K + H120D | 91 | 90 | A |
| E251K + D181N | 134 | 74 | B |
| E251K + E271Q | 118 | 59 | B |
| Q271E + H120D | 73 | 137 | C |
| D120H + D181N | 137 | 71 | B |
| D120H + E271Q | 137 | 73 | B |
| N181D + K235L | 79 | 128 | C |
| E195G + A222M + R170Y | 70 | 65 | A |
| E195G + A222M + E136R | 70 | 59 | A |
| H120D + G195E + K235L + K251E | 89 | 95 | A |
| H120D + R170Y + K235L + K251E | 109 | 61 | B |
| *36D + H120D + R170Y + G195E | 56 | 103 | C |
| *36D + R170Y + G195E + K235L | 40 | 82 | C |
| H120D + R170Y + G195E + K235L + K251E | 90 | 45 | B |
| *36D + H120D + R170Y + G195E + K235L | 73 | 19 | B |
| H120D + R170Y + A222M + K235L + K251E | 72 | 82 | A |
| *36D + H120D + R170Y + G195E + K235L, E251K | 76 | 82 | A |
| R136E + H120D + R170Y + G195E + K235L + K251E | 75 | 73 | A |
| Q271E + *36D + H120D + R170Y + G195E + K235L | 50 | 95 | B |
| D36* + D120H + Y170R + E195G + L235K + D181N | 117 | 41 | B | forward exchange: amino acid exchange as listed to the left.
reverse exchange: amino acid exchange opposite to the listed.
type:
A = exchanges gives nearly equal effect i both directions.
B = the reverse exchange is more important
C = the forward exchange is more important
for all: if different from 100 this amino acid position is included in an epitope.
if <100 the epitope change means need for more antibody to give a response equal to the reference reaction.
if >100 the epitope change means that there is a heteroclitic effect (affinity increase to this epitope).

The interpretation of these results are discussed in detail below in the concluding remarks.

Series D:

Again one protein was used for coating the wells in ELISA plates. Furthermore only one sera pool was tested as the reference. This serum was tested in only one dilution.

Before the sera were added to the coated wells, they were preincubated with the wild type or variant of the protein in another set of wells.

In these other wells dilution series of wild type or variants were incubated with the same concentration of the reference. Each well therefore contained serum plus either wild type or variant in a specific dilution from a dilution series.

The protein concentrations, were selected to assure a surplus of antigen in one end of the dilution series, and nearly no reaction in the other end. Consequently the protein can in some wells block all rat anti-protein reactivity, if it corresponds in specificity. In other wells more and more rat antibody will remain unreacted. If the co-incubated protein is very different from the one used to produce the rat antibodies, unreacted antibodies will remain in all wells, independent of the concentration used.

After the co-incubation of sera plus diluted proteins, the reacted mixture was transfered to the coated wells.

If rat antibody activity is left over it will bind to the coated protein in the wells, and eventually the rat antibodies are bound by peroxidase labelled anti rat(IgX) antibodies, and development performed as above in Series A.

The results in this assay indicate whether the co-incubated protein is related to the coated or not. Both with respect to epitope identity (partly or fully) or epitope presence.

The variants used in this series are indicated below in TABLE IV:

TABLE IV

Subtilisin 309 variants used in Series D
Changes in amino acid sequence compared to WT:

| WT | |
|---|---|
| SP436 | G195E+M222A |
| SP458 | M222A |
| S001) | G195E |
| S003) | R170Y |
| S005) | K251E |
| S006) | H120D |
| S012) | R170Y+G195E+K251E |
| S015) | K235L |
| S019) | H120D+R170Y+G195E+K235L |
| S020) | H120D+R170Y+G195E+K235L+K251E |
| S021) | *36D |
| S022) | *36D+R170Y+G195E+K251E |
| S023) | *36D+H120D+R170Y+G195E+K235L |
| S024) | *36D+H120D+R170Y+G195E+K235L+K251E |
| S025) | *36D+H120D+G195E+K235L |
| S026) | E136R |
| S027) | E89S |
| S028) | D181N |
| S033) | E271Q |
| S046) | Y209L |

One sera group was used per assay, consisting of 22 subassays. In each sub-assay the sera were absorbed in liquid phase with wt or one of the variants in a dilution series. Finally the remaining antibodies were tested towards one and the same protein all over.

Each sub-assay therefore results in removing antibody reactivity and estimating what is left over. In this set up one sera group is being absorbed with all 21 proteins, and finally tested with the same type originally used for immunization.

Loss of epitopes in the absorbed protein compared to the tested protein will mean positive results even with the highest concentration of absorbing protein. As indicated in FIGS. 1 to 6 the plots will for such variants level off not reaching the full effect seen in the reference absolute absorbtion.

Change of epitopes can mean lowering of binding strength. Therefore the sub-assay plots will be positioned different on the concentration axis, giving a titer difference in comparison with the reference absolute absorbtion.

So far only antisera to SP436 have been tested.

In FIGS. 1 through 6 the effect of absorbtion is plotted. The first well is without any variant or wt to absorb, i.e. an internal control. The following wells contain increasing concentrations of absorbing protein.

There is basically two types of plots. One is with decreasing values all over. Another is levelling off, leaving some response even in the presence of the highest concentration of absorbing protein. The first type will correspond to change of epitopes, whereas the second type will correspond to loss of epitope (meaning a general lowering of binding energy, enabling a high degree of reversibility in antibody binding).

From FIGS. 1 through 6 it is obvious that the following S numbers "level off": S003, S012, S019, S020, S022, S023, S024 and S026. S026 contains the variant E136R and is the only variant in that position tested, therefore S026 is not included fully in the evaluation.

In TABLE V the effect of absorbtion is listed for all 21 proteins including the reference SP436 sorted in three parts.

The first part gives the effect of an amino acid change in position nos. 195 and 222, and combinations with other single position changes.

The second part gives change of position no. 170 in combination with all other tested changes.

The third part gives change of position no. 251 in combination with all other tested changes.

The test serum was serum group no 1 (anti-SP436).

Results are measured as titer at one fixed read-out value, and recalculated to the absorbing capacity relative to the reference (in percent).

TABLE V

SERIES D, coat: SP436, sera group no. 1
All values are relative to sera group no 1 (=ref.).
All values are absorbance capacity relative to the reference.

| Variant | IgG v.40NSVU | IgE v.40NSVU | Amino acid exch. rel. to SP 436 |
|---|---|---|---|
| SP458 | 70 | 59 | 195 |
| S001 | 70 | 87 | 222 |
| WT | 9 | 10 | 195, 222 |
| S021 | 27 | 31 | 36, 195, 222 |
| S027 | 104 | 380 | 89, 195, 222 |
| S006 | 26 | 30 | 120, 195, 222 |
| S026 | 0 | 0 | 136, 195, 222 |
| S003 | 26 | 40 | 170, 195, 222 |
| S028 | 102 | 220 | 181, 195, 222 |
| S046 | 120 | 150 | 195, 209, 222 |
| S015 | 30 | 36 | 195, 222, 235 |
| S005 | 74 | 67 | 195, 222, 251 |
| S033 | 74 | 29 | 195, 222, 271 |
| S003 | 26 | 40 | 170, 195, 222 |
| S012 | 14 | 20 | 170, 222, 251 |
| S019 | 23 | 125 | 120, 170, 222, 235 |
| S020 | 20 | 88 | 120, 170, 222, 235, 251 |
| S022 | 4 | 11 | 36, 170, 222, 251 |
| S023 | 4 | 4 | 36, 120, 170, 222, 235 |
| S024 | 2 | 6 | 36, 120, 170, 222, 235, 251 |
| S005 | 74 | 67 | 195, 222, 251 |
| S012 | 14 | 20 | 170, 222, 251 |
| S020 | 20 | 88 | 120, 170, 222, 235, 251 |
| S022 | 4 | 11 | 36, 170, 222, 251 |
| S024 | 2 | 6 | 36, 120, 170, 222, 235, 251 |

Results of Series D.

Taking amino acid change one by one from TABLE V, absorbtion capacity being compared to the reference:

(ND=not distinguishable in present set-up)

| | |
|---|---|
| No. 36: | |
| with 195 + 222 (S021) | ND |
| with 170 + 222 + 251 (S022) | ND |
| with 120 + 170 + 222 + 235 (S023) | absorb less IgE |
| with 120 + 170 + 222 + 235 + 251 (S024) | absorb less IgE |
| No. 89: | |
| with 195 + 222 (S027) | absorb more IgG , and absorb much more IgE |
| No. 120: | |
| with 195 + 222 (S006) | ND |
| no. 170: | |
| with 195 + 222 (S003) | ND |
| no. 181: | |
| with 195 + 222 (S028) | absorb more IgG, and absorb much more IgE |
| No. 195: | |
| alone (SP 458) | absorb little less IgG, and absorb little less IgE |
| with 222 (SP 436) | absorb much less IgG, and absorb much less IgE |
| No. 222: | |
| alone (S001) | absorb little less IgG, and absorb little less IgE |
| No. 235: | |
| with 195 + 222 (S015) | ND |
| No. 251: | |
| with 195 + 222 (S005) | absorb little more IgG, and absorb little more IgE |
| with 36 + 120 + 170 + 222 + 235 (S024) | ND |
| no. 271: | |
| with 195 + 222 (S033) | absorb more IgG |

The results must be compared with data in TABLE VI, where the inter-atomic distances between $C_\alpha$'s are listed.

The epitope size is typically 10–15 Å in radius, and the amino acids are exposed like in a field.

Combining this information with a 3-dimensional (3D) view, it will be possible to estimate which amino acids belong to the same epitope, and therefore will be bound by the same antibody.

TABLE VI

INTERATOMIC DISTANCES BETWEEN C$_\alpha$'s in Å

| AA no. | 36 | 89 | 120 | 136 | 170 | 181 | 195 | 209 | 222 | 235 | 251 | 271 |
|---|---|---|---|---|---|---|---|---|---|---|---|---|
| 36 | 0 | 13.6 | 18.2 | 23.5 | 27.3 | 26 | 30.6 | 8.5 | 15.6 | 24.3 | 29.7 | 28.6 |
| 89 | 13.6 | 0 | 9.9 | 25.9 | 26.8 | 27.6 | 28.4 | 18.3 | 18.5 | 12.6 | 23.3 | 20.7 |
| 120 | 18.2 | 9.9 | 0 | 18.4 | 20.3 | 27.8 | 21.6 | 24.4 | 19.5 | 8.5 | 17.6 | 20.2 |
| 136 | 23.5 | 25.9 | 18.4 | 0 | 9.4 | 29.8 | 14.3 | 30.6 | 22.7 | 24.5 | 22.1 | 32 |
| 170 | 27.3 | 26.8 | 20.3 | 9.4 | 0 | 22 | 5.9 | 28.6 | 17.8 | 23.7 | 16.4 | 27.2 |
| 181 | 26 | 27.6 | 27.8 | 29.8 | 22 | 0 | 20.5 | 20.9 | 11.1 | 26.5 | 18.9 | 19.3 |
| 195 | 30.6 | 28.4 | 21.6 | 14.3 | 5.9 | 20.5 | 0 | 31 | 18.9 | 23 | 12.5 | 24.4 |
| 209 | 8.5 | 18.3 | 24.4 | 30.6 | 28.6 | 20.9 | 31 | 0 | 12.8 | 27 | 29.7 | 27.2 |
| 222 | 15.6 | 18.5 | 19.5 | 22.7 | 17.8 | 11.1 | 18.9 | 12.8 | 0 | 20.9 | 18.4 | 19.6 |
| 235 | 24.3 | 12.6 | 8.5 | 24.5 | 23.7 | 26.5 | 23 | 27 | 20.9 | 0 | 14.2 | 13.4 |
| 251 | 29.7 | 23.3 | 17.6 | 22.1 | 16.4 | 18.9 | 12.5 | 29.7 | 18.4 | 14.2 | 0 | 12.8 |
| 271 | 28.6 | 20.7 | 20.2 | 32 | 27.2 | 19.3 | 24.4 | 27.2 | 19.6 | 13.4 | 12.8 | 0 |

Distances to/from no 36 are estimated as mean of (35+37) as the subtilisin 309 database does not include 3D coordinates of no 36 (not present in wt).

Initially nos 120+235 seem to cooperate in one epitope, and nos 195+251 in another epitope.

Furthermore nos 89 and 181 both will give much higher absorbtion of both IgE and IgG. No 251 little more of both, and no 271 little more of IgG.

Amino acid no 170 is changed in all the other cited nos.,—leading to loss of epitope. Even the highest concentration of these proteins will not remove all antibodies from the preparation.

This single epitope accounts for approximately 30% of the reactivity, therefore it can be expected that the total number of epitopes is low.

Figure 4:
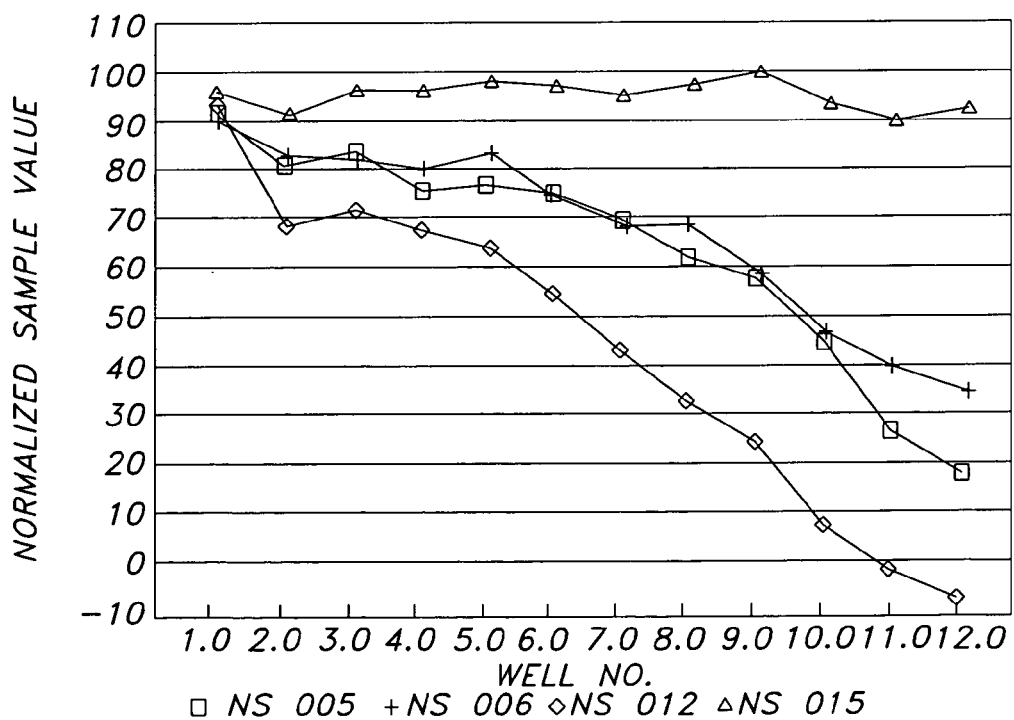
Figure 5:
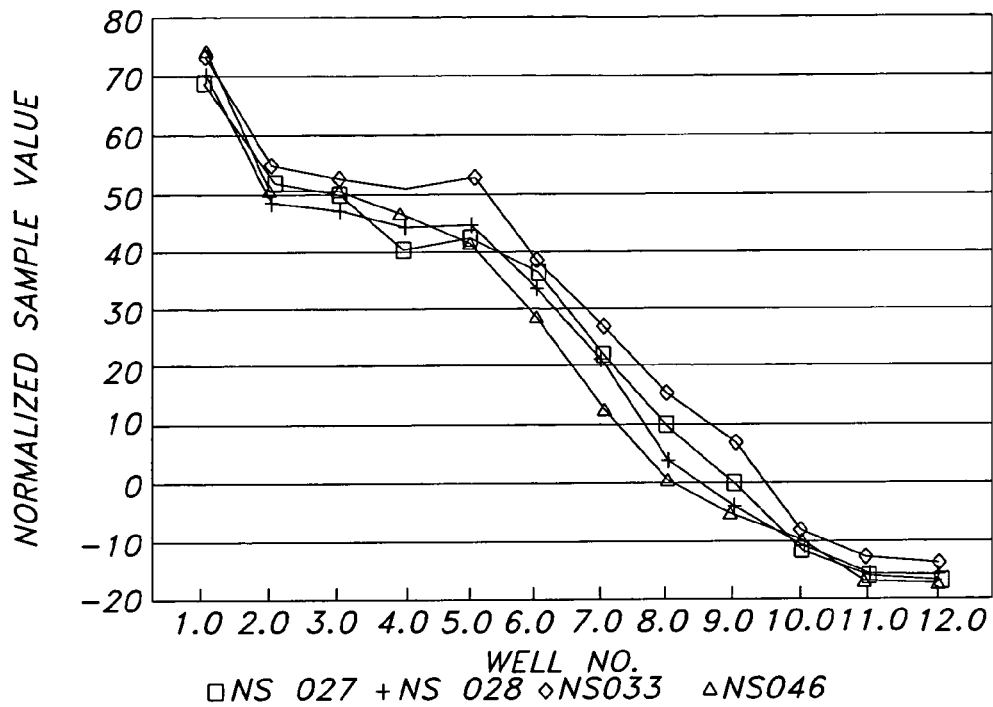
Figure 6:
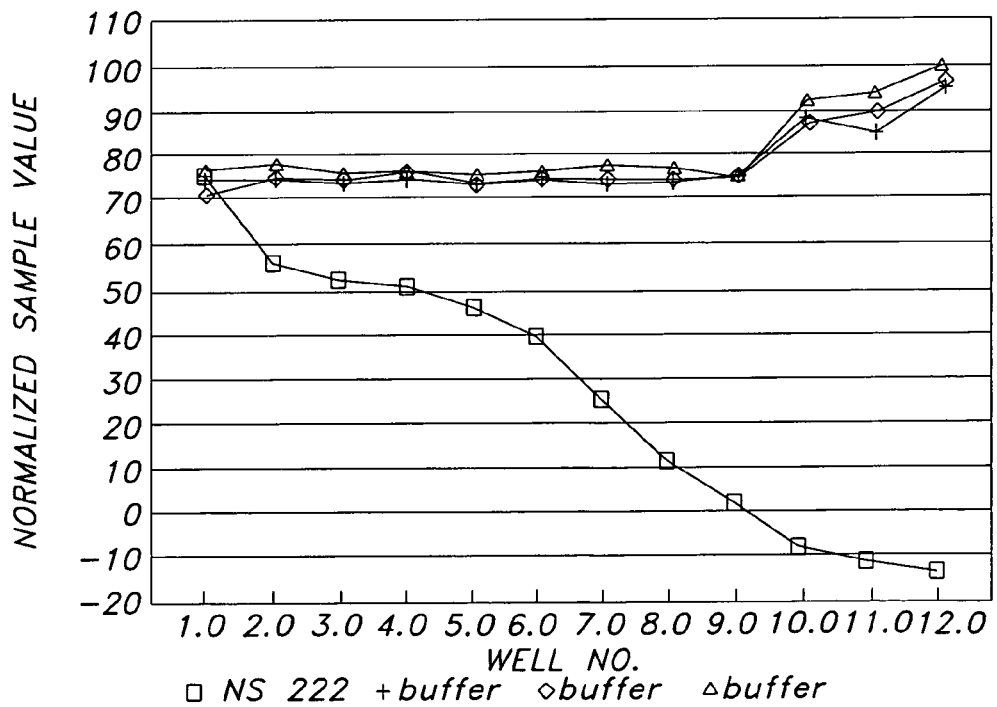

Also, it seems as if position 136 is connected with a major epitope (cf FIG. 4). Since S026 is the only variant wherein position 136 is changed, a definite conclusion must await further study.

In TABLE VII below the probability for pairs of positions investigated here belonging to the same epitope is indicated.

It is expected that changes in the charged amino acid residues will entail the greatest effect on the immunological potential of subtilisin 309'.

Concluding Remarks

SERIES A, the "data extraction" pages, TABLE III, list results from amino acid (AA) exchanges both ways i.e. there are sera towards both variants in TABLE III, and these have been tested with their immunogen and other variants comprising changes in the same position(s).

Looking at changes from WT to a variant the following effects are seen:

In the following the terms "essential", "critical", and "present" are used in connection with the amino acids in specified positions. These expressions have the meanings as defined in Geysen et al. Science 135 (1987)1184–90.

I. AA no. 120 is not "essential" in WT but becomes so in the variant.

AA no. 235 same as for 120!

AA no. 271 same as for 120!

II. AA no. 251 is "essential" in WT but not in variant.

TABLE VII

PROBABILITY FOR BEING IN THE SAME EPITOPE (<9.9 Å: high.10–15 Å: medium)

| AA no. | 36 | 89 | 120 | 136 | 170 | 181 | 195 | 209 | 222 | 235 | 251 | 271 |
|---|---|---|---|---|---|---|---|---|---|---|---|---|
| 36 | | medium | | | | | high | | | | | |
| 89 | | | high | | | | | | | medium | | |
| 120 | | | | | | | | | | high | | |
| 136 | | | | | high | | medium | | | | | |
| 170 | | | | | | | high | | | | | |
| 181 | | | | | | | | | medium | | | |
| 195 | | | | | | | | | | | medium | |
| 209 | | | | | | | | | medium | | | |
| 222 | | | | | | | | | | | | |
| 235 | | | | | | | | | | | medium | medium |
| 251 | | | | | | | | | | | | medium |
| 271 | | | | | | | | | | | | |

From the above the following amino acid residues are selected for being changed in order to influence the immunological potential of subtilisin 309.

non-polar: 129, 131, 151, 152, 162, 168, 169, 172, 174, 175, 176, 194, 196, polar: 127, 128, 130, 153, 154, 161, 163, 167, 171, 173, 193, 195, charged: 136, 170, 186, 197, 247, 251, 261, III. AA no. 181 is showing heteroclitic effect in change D181N and is "essential" in backwards change N181D.

IV. AA no. 136 is giving big impact on response both ways of exchange.

AA no. 170 same as for 136.

AA no. 195 same as for 136.

The following exchange data can be segmented in more or less two groups (of 13 and 11 respectively):

V. Rows 9, 11, 12, 13, 14, 15, 17, 19, 20, 21, 26, 27 and 32 exhibits effects that would be expected from the calculated accumulated effects in single mutations.

VI. Rows 10, 16, 18, 22, 23, 24, 25, 28, 29, 30, and 31 exhibit effects that would be not expected from calculated accumulated effects in single mutations.

It is noted that V. and VI. have been calculated without including AA no. 36, as there are no two-way data on this change. Therefor rows 24, 25, 27, 29 and 32 may in subsequent calculations including AA no. 36 exchange come out differently.

All AA's with data both ways line up as participants in some epitope. Their impact on recognition and binding by antibodies are largely different, but none are without any effect.

Groups I. and II. illustrate how some AA's are non-essential, whereas other in the same positions are essential.

From this it seems as if the tested changes in AA's 120, 235 and 271 create essential AA's, maybe even epitopes in the variants.

Also, it seems as if change of no 251 removes an essential AA.

This may in humans lead to a reduced allergenic reaction to the new variant as compared to the reaction to the wild type enzyme. After production of new antibodies towards the variant molecule, there may still be a low reaction that anyhow should be restored with full strenght upon switch back to WT exposure (both by anti-WT and anti-variant antibodies).

The most interesting group is III. where change of no.-181 gives a heteroclitic effect (i.e. the anti-WT sera reacts stronger with the variants than with its own WT immunogen), and this AA seems to be essential to the anti-variant sera.

Therefore this seems to be a very important position, which upon change can create increased response, not only in individuals that are exposed to the molecule on a first-time-basis, but also individuals already having antibodies towards the WT enzyme can be expected to react even stronger with the variant.

This means that from an immunological view a change in this position should be avoided.

The group IV, shows changes providing antisera that both ways react strongest with their own immunogen. A change in both ways exhibits decreased response, and the responses are restored upon returning to their own immunogen.

This may in humans mean an immediate lowering of response upon switch to variant, but as new anti-variant antibodies appear the response may be restored.

From an immunological viewpoint these changes seem to be neutral or even beneficial.

The remaining rows in Table III partly confirms the above, and partly illustrate that simple accumulation of effects cannot be expected in multiple AA exchange variants. Further analysis is needed to confirm any accumulation of immunological effects.

Using molecules wherein a single or a few amino acids have been changed the following effects were found:
1. In specific positions certain amino acids seems not to be essential to the epitope, whereas other may be.
2. In specific positions all tested amino acids seem to be essential to the epitope.
3. Exchange of one amino acid for another can give a heteroclitic effect. Furthermore the new amino acid may be essential to the "variant" molecule.

From these findings the following responses (incl symptoms) may be seen, if an individual already sensitive to the molecule of origin is exposed to the altered molecule(s)

i No change immediately, but shortly later an increased response. Upon switch to exposure to molecule of origin the response is restored.

ii Lowering of the response upon change. Upon switch back to exposure to molecule of origin restoration of response.

iii Increase in response upon change. Upon switch back to exposure to molecule of origin an immediate drop is seen, that finally resumes the original strenght of response before the change to the variant.

iv Initially a drop in response, that is being restored.
Upon switch back to molecule of origin a drop in response that very soon is being restored.

From an immunological view the preferred switch will be of the group II type, but also a group IV type of change is acceptable.

Although the present invention has been illustrated in connection with certain specific embodiments, this is in no way to be construed that it should be limited to these embodiments, the invention being defined by the appended claims and the whole of the specification.

What is claimed is:

1. A method for selecting a variant enzyme of a reference enzyme, wherein the variant enzyme causes a lower immunogenic response in a mammal than the reference enzyme, comprising:
   (a) (i) preparing a recombinant expression vector comprising a DNA sequence encoding the reference enzyme;
      (ii) transforming a host cell with the vector and expressing the reference enzyme in the host cell;
      (iii) isolating the reference enzyme from the host cell;
      (iv) immunizing an animal with the reference enzyme; and
      (v) isolating antibodies reactive with the reference enzyme from the animal;
   (b) (i) preparing recombinant vectors comprising DNA sequences encoding one or more variant enzymes, wherein the one or more variant enzymes differ from the reference enzyme by one or more amino acid substitutions at one or more positions in the amino acid sequence of the reference enzyme;
      (ii) transforming host cells with the vectors and expressing the variant enzymes in the host cells;
      (iii) isolating the variant enzymes from the host cells;
      (iv) immunizing animals with the variant enzymes; and
      (v) isolating antibodies reactive with the one or more variant enzymes;
   (c) mapping one or more epitopes of the reference enzyme with immunological techniques by incubating the antibodies raised in steps (a) and (b) with the reference enzyme and at least one of the one or more variant enzymes; and
   (d) selecting a variant enzyme, which (i) has an altered amino acid sequence of one or more epitopes of the reference enzyme, (ii) has enzymatic activity, and (iii) evokes a lower immunogenic response in an animal than the reference enzyme.

2. The method of claim 1, wherein the reference enzyme is a detergent enzyme.

3. The method of claim 2, wherein the detergent enzyme is an amylase, a cellulase, a lipase, an oxidase, or a protease.

4. The method of claim 1, wherein the reference enzyme is an amylase, a cellulase, a lipase, or a lyase.

5. A method for selecting a variant enzyme of a reference enzyme, wherein the variant enzyme causes a lower immunogenic response in a mammal than the reference enzyme, comprising:
   (a) (i) preparing a recombinant expression vector comprising a DNA sequence encoding the reference enzyme;
   (ii) transforming a host cell with the vector and expressing the reference enzyme in the host cell;
   (iii) isolating the reference enzyme from the host cell;
   (iv) immunizing an animal with the reference enzyme;
   (v) isolating cells producing antibodies reactive with the reference enzyme from the animal; and
   (vi) using said antibody-producing cells to prepare polyclonal antibodies against the reference enzyme;
   (b) (i) preparing recombinant vectors comprising DNA sequences encoding one or more variant enzymes, wherein the one or more variant enzymes differ from the reference enzyme by one or more amino acid substitutions at one or more positions in the amino acid sequence of the reference enzyme;
   (ii) transforming host cells with the vectors and expressing the variant enzymes in the host cells;
   (iii) isolating the variant enzymes from the host cells;
   (iv) immunizing animals with the variant enzymes;
   (v) isolating cells producing antibodies reactive with the variant enzymes from the animals; and
   (vi) using said antibody-producing cells to prepare polyclonal antibodies reactive with the one or more variant enzymes;
   (c) mapping one or more epitopes of the reference enzyme with immunological techniques by:
   (i) incubating the polyclonal antibodies prepared in steps (a) and (b) with the reference enzyme and with at least one variant enzyme; and
   (ii) incubating the mixture from step (i) with another enzyme selected from the group consisting of the reference enzyme and a variant enzyme;
   (d) selecting a variant, which (i) has an altered amino acid sequence of one or more epitopes of the reference enzyme, (ii) has enzymatic activity and (iii) evokes a lower immunogenic response in an animal than the reference enzyme.

6. The method of claim 5, wherein the reference enzyme is a detergent enzyme.

7. The method of claim 6, wherein the detergent enzyme is an amylase, a cellulase, a lipase, an oxidase, or a protease.

8. The method of claim 5, wherein the reference enzyme is an amylase, a cellulase, a lipase, or a lyase.

* * * * *